United States Patent
Rowney et al.

(10) Patent No.: US 9,662,368 B2
(45) Date of Patent: May 30, 2017

(54) FORMULATION COMPRISING WHEY PROTEIN AND HYDROLYSATES FOR IMPROVING MUSCLE RECOVERY

(75) Inventors: Michelle Rowney, Port Campbell (AU); Andrew Brown, Cobram (AU); Yu Pan, Hoppers Crossing (AU); Jonathan David Buckley, Aberfoyle Park (AU)

(73) Assignee: MURRAY GOULBURN CO-OPERATIVE., LIMITED, Southbank, Victoria (AU)

(*) Notice: Subject to any disclaimer, the term of this patent is extended or adjusted under 35 U.S.C. 154(b) by 733 days.

(21) Appl. No.: 12/304,356

(22) PCT Filed: Jun. 15, 2007

(86) PCT No.: PCT/AU2007/000841
§ 371 (c)(1),
(2), (4) Date: May 4, 2009

(87) PCT Pub. No.: WO2007/143794
PCT Pub. Date: Dec. 21, 2007

(65) Prior Publication Data
US 2009/0298767 A1    Dec. 3, 2009

(30) Foreign Application Priority Data
Jun. 15, 2006 (AU) .............................. 2006903232

(51) Int. Cl.
*A61K 38/18* (2006.01)
*A61K 38/01* (2006.01)
*A23L 33/18* (2016.01)
*A23L 33/19* (2016.01)

(52) U.S. Cl.
CPC ............ *A61K 38/018* (2013.01); *A23L 33/18* (2016.08); *A23L 33/19* (2016.08)

(58) Field of Classification Search
CPC ...................................................... A61K 8/97
See application file for complete search history.

(56) References Cited

U.S. PATENT DOCUMENTS

| | | | |
|---|---|---|---|
| 6,784,209 B1 * | 8/2004 | Gardiner et al. ............ | 514/565 |
| 2003/0022817 A1 * | 1/2003 | Berthelsen et al. ............ | 514/2 |
| 2006/0073186 A1 | 4/2006 | Kume et al. | |
| 2006/0193949 A1 | 8/2006 | Portman | |

FOREIGN PATENT DOCUMENTS

| | | |
|---|---|---|
| EP | 1034704 A1 | 9/2000 |
| JP | 2004-182630 | 7/2004 |
| NZ | WO 0219837 A1 * 3/2002 ............ A23J 3/343 |
| WO | WO 92/21248 A1 | 12/1992 |
| WO | WO 97/39641 A1 | 10/1997 |
| WO | WO 99/49741 A1 | 10/1999 |
| WO | WO 99/65326 A1 | 12/1999 |
| WO | WO 2004-049830 A1 | 7/2004 |
| WO | WO 2004/056207 A1 | 7/2004 |

OTHER PUBLICATIONS

Bodybuilding.com, "Nature's Best VHT Only Whey". Internet Archive Date: Mar. 9, 1999 [Retrieved from the Internet on: Mar. 18, 2011]. Retrieved from <URL:http://replay.waybackmachine.org/19990903034558/http://bodybuilding.com/store/nb/whey.html>.*
van Hall et al. "Muscle glycogen resynthesis during recovery from cycle exercise: no effect of additional protein ingestion". J Appl Physiol, vol. 88, No. 5 (May 2000)1631-1636, Abstract.*
Notification of the First Office Action corresponding to Chinese Application No. 200780021776.X issued Jun. 30, 2011.
U.S. Appl. No. 11/782,250, filed Jul. 24, 2007, Rowney et al.
Derwent Abstract Accession No. 2004-415801/39, JP2004155751A (Meiji Milk Prod. Co., Ltd.) Jun. 3, 2004.
Buckley et al. "International Society of Sports Nutrition Conference Proceedings", *J. Int. Soc. Sports Nutrition*. 31(1):S1-S29 (2006).
International Search Report corresponding to International Application No. PCT/AU2007/000841 mailed Aug. 13, 2007.
Gobbetti et al. "Latent Bioactive Peptides in Milk Proteins: Proteolytic Activation and Significance in Dairy Processing", *Critical Reviews in Food Science and Nutrition* 42(3):223-239 (2002).
Korhonen et al. "Bioactive peptides: Production and functionality", *International Dairy Journal* 16:945-960 (2006).
Moller et al. "Bioactive peptides and proteins from foods: Indication for health effects", *Eur. J. Nutr.* 47:171-182 (2008).
Vermeirssen et al. "Bioavailability of angiotensin I converting enzyme inhibitory peptides", *British Journal of Nutrition* 92:357-366 (2004).
Creusot et al. "Peptide-peptide and protein-protein interactions in mixtures of whey protein isolate and whey protein isolate hydrolysates", *International Dairy Journal* 16:840-849 (2006).
Supplementary European Search Report corresponding to European Application No. 07719083.3 dated Feb. 3, 2010.
Office Action corresponding to Japanese Application No. 2009-514596 dated Jun. 12, 2012.

* cited by examiner

*Primary Examiner* — Amy L Clark
(74) *Attorney, Agent, or Firm* — Drinker Biddle & Reath LLP (57) ABSTRACT

The present invention relates to a formulation comprising whey protein or a hydrolysate of whey protein, which formulation is capable of inhibiting the expression of TNFα in lipopolysaccharide-stimulated macrophages in vitro. Also provided are uses of the formulation for attenuating a reduction in muscle function which results from muscle damage and/or for enhancing recovery from muscle damage and/or for enhancing the force generating capacity of muscle and methods of making the formulation.

12 Claims, 7 Drawing Sheets

Figure 7

US 9,662,368 B2

FORMULATION COMPRISING WHEY PROTEIN AND HYDROLYSATES FOR IMPROVING MUSCLE RECOVERY

RELATED APPLICATIONS

The present application is a 35 U.S.C. §371 national phase application of PCT International Application No. PCT/AU2007/000841, having an international filing date of Jun. 15, 2007 and claiming priority to Australian Patent Application No. 2006903232, filed Jun. 15, 2006. The disclosure of each application is incorporated herein by reference in its entirety. The above PCT International Application was published in the English language and has International Publication No. WO 2007/143794A1.

FIELD

The present invention relates to formulations for improving muscle recovery, especially after exercise. More specifically, it relates to such formulations containing whey protein and hydrolysates.

BACKGROUND

The high mechanical forces experienced by skeletal muscle during intense exercise, particularly eccentric exercise, can induce mechanical damage which is followed by an acute inflammatory response, the development of pain and a loss of force-generating capacity.

Interventions capable of reducing muscle damage and/or inflammation or accelerating tissue repair have the potential to speed recovery of muscle force generation following exercise. They may also be able to assist in muscle recovery following illness.

SUMMARY

In a first aspect there is provided a formulation comprising whey protein or a hydrolysate of whey protein, wherein the formulation is able to inhibit the expression of TNFα in lipopolysaccharide-stimulated macrophages in vitro.

In another aspect there is provided a formulation comprising a hydrolysate of whey protein wherein the formulation is able to inhibit the expression of TNFα in lipopolysaccharide-stimulated macrophages in vitro.

In one embodiment, the formulation is a nutraceutical formulation.

In particular embodiments of these preceding aspects the hydrolysate is an enzyme hydrolysate. In particular embodiments the enzyme is of bacterial or fungal origin, and preferably a metalloproteinase. In some embodiments the enzyme is selected from the group consisting of an enzyme from the IUBMB Enzyme Nomenclature class EC 3.4.24.28, including Neutrase®, Protease N "Amano", and Corolase N and an enzyme from the IUBMB Enzyme Nomenclature class EC 3.4.21.62, including Alcalase® Subtilisin A (Type VIII) and Optimase.

Yet another aspect provides use of a formulation comprising a hydrolysate of whey protein for attenuating a reduction in muscle function which results from muscle damage and/or for enhancing recovery from muscle damage and/or for enhancing the force generating capacity of muscle.

In certain embodiments of any of the preceding aspects, the formulation consists essentially of a hydrolysate of whey protein.

Another aspect provides use of a hydrolysate of whey protein in the preparation of a nutraceutical medicament for attenuating a reduction in muscle function which results from muscle damage and/or for enhancing recovery from muscle damage and use of a hydrolysate of whey protein in the preparation of a nutraceutical medicament for enhancing the force generating capacity of muscle.

Also provided is a method of preparing a formulation for attenuating a reduction in muscle function which results from muscle damage and/or enhancing recovery from muscle damage and/or for enhancing the force generating capacity of muscle, the method comprising hydrolysing whey protein to produce a formulation comprising whey protein hydrolysate.

BRIEF DESCRIPTION OF THE FIGURES

In the following examples, reference will be made to the accompanying figures as follows:

FIG. 1 is a schematic diagram setting out the timeline for the experiments described in Example 4. The timeline demonstrates the periods at which samples were taken from each subject and at muscle function assessed relative to the induction of muscle damage by exercise. The timeline also demonstrates the times at which each subject was given a supplement.

FIG. 2 provides in graphical form the results of the muscle peak isometric torque testing described in Example 4. "A" represents a placebo supplement, "B" represents the WPI hydrolysate supplement, "C" represents the WPI supplement and "D" represents Casein-containing supplement. The results demonstrate that subjects supplemented with hydrolysed WPI produced a significantly higher peak isometric force than subjects having any of the other treatments, and that at 24 hours the subjects supplemented with hydrolysed WPI produced a peak isometric force significantly greater than baseline values. Peak isometric torque assessed at baseline (0 hours), immediately after 100 maximal eccentric contractions, and at 1, 2, 6 and 24 hours after.
* significantly different from baseline (P=0.03) and from all other treatments (P<0.001).
† significantly different from baseline for supplements A and C (P<0.05).

DETAILED DESCRIPTION

The present inventors have examined the biological activities provided by various milk fractions.

The inventors have identified that Whey Protein Isolate (WPI), a milk fraction which contains whey proteins and which may be obtained from a variety of sources, including cheese whey and acid/casein whey, possesses an anti-inflammatory activity as identified by an in vitro assay of TNFα expression inhibition. They have also identified that particular hydrolysates of WPI unexpectedly have an increase in this anti-inflammatory activity. Certain hydrolysates of WPI also have increased ability to stimulate the growth of fibroblasts in vitro as compared to WPI.

The inventors have further identified that administration of WPI and certain enzyme hydrolysates of WPI are able to attenuate symptoms of muscle damage and promote the recovery of muscle function in subjects after muscle-damaging exercise. This allows athletes to return to competition or training more rapidly after exercise. The activity of the hydrolysates is greater than the activity possessed by the corresponding non-hydrolysed form of WPI. Certain WPI hydrolysates were also able to enhance the muscle force generating ability in subjects subjected to muscle-damaging exercise.

In one embodiment the WPI comprises:

| | |
|---|---|
| Moisture | 5.0% |
| Fat | 0.5% |
| pH (5% solution) | 6.3 |
| Ash | 3.7% |
| Lactose | 0.5% |
| Protein (TN × 6.38) | 90.0% |
| Phosphorous | 0.3% |
| Calcium | 0.15% |

In a particular embodiment, the formulation which comprises WPI or a hydrolysate of WPI does not also contain glutamine. In another embodiment the formulation does not also contain any additional branched chain amino acids (BCAAs) such as isoleucine, leucine and valine. In another embodiment the formulation does not also contain an additional source of free or enriched amino acids such as carnitine, arginine, tyrosine or histidine. In another embodiment the formulation does not also contain an additional non-whey source of lipid. In another embodiment the formulation does not also contain an additional source of protein which is not derived from milk such as soy protein, rice protein, pea protein, carob protein, oat protein, a hydrolysate thereof and/or a mixture thereof. In another embodiment the formulation does not also contain any one or more of an additional source of protein.

Milk is a complex mixture of molecules, including numerous polypeptides, lipids and fats, and carbohydrates. The polypeptide component, while dominated by casein, contains many other proteins having diverse functions, such as α-lactalbumin, β-lactoglobulin, immunoglobulins and caseinoglycomacropeptide.

Throughout the specification the term "milk fraction" refers to a formulation which is ultimately derived from milk and which is at least enriched in one or more constituents found in whole milk. In the context of the present specification, a "milk fraction" is one which contains non-casein proteins found in milk. Whey or "milk plasma" is a common milk fraction which remains after the process of "curdling" has removed much of the casein and milk fat component from whole milk or skim milk.

"Milk fraction" includes fractions which have been enriched for specific components or combinations of components of milk. The milk fraction "Whey protein isolate" (WPI) for instance is one in which the non-casein protein components of milk have been enriched when compared with whole milk.

"Whey protein" comprises one or more protein(s) which are found in whey and which, when hydrolysed, possesses the desired biological activity described herein. Different sources of whey protein are contemplated. In particular whey protein originating from sweet whey or from acid whey have both been demonstrated to possess similar activity. There are, for example, numerous methods for the production of whey, for instance as by-products arising during the production of different forms of cheese or as a by-product of the casein making process, and each of these will produce whey with a somewhat different formulation.

The principal proteins found in whey are α-lactalbumin and β-lactoglobulin and caseinoglycomacropeptide (CGMP), the latter forming about 25% of protein present in cheese whey WPI. Milk fractions which contain one or more of these proteins are contemplated for use as starting materials for the hydrolysis methods described herein, although fractions which do not contain these proteins are not expressly excluded as possible sources of starting material.

Although the exemplified method provided herein utilises WPI as a starting material for hydrolysis, it is to be understood that other milk fractions or whole milk which also contain components of milk which are found in whey or WPI could be substituted in place of WPI without significantly altering the desired biological properties possessed by the end-product. For instance, whole milk or milk protein concentrates will contain the same components, including proteins, which are found in whey, albeit in a more dilute form. The components which are found in whey may also be found in non-whey milk fractions, albeit possibly in a more dilute form.

It may prove desirable to remove or reduce particular components of milk or milk protein concentrates, for example to increase the specific activity of the biologically active components. Techniques to reduce the water, fat, lactose and "ash" (which comprises the mineral components of milk) content of milk products are well known in the art, and it is anticipated that these techniques will increase the specific activity of the desired biologically active components.

In some embodiments it may also prove desirable to reduce the content of casein present in the milk protein fractions. Casein, if present, may potentially dilute the bioactivity derived from whey, and may form a curd if there is an enzyme deactivation step during hydrolysis. Techniques for the removal of casein from milk products, such as curdling using isoelectric precipitation with acid, or using enzymes such as rennet, are well known in the art.

Similarly, whey protein may be concentrated by a variety of methods not limited to the preparation of WPI, such as the methods used to prepare commercially available whey protein concentrate (WPC). WPC contains many of the components which are found in WPI, although in different proportions, and consequently it is anticipated that WPC will also possess the activity demonstrated in WPI. Any precursor of WPI, including intermediate products of the process of producing WPI, could be a starting material for hydrolysis, although the specific activity would be lower than that of WPI and the resulting hydrolysate may require subsequent purification steps.

In particular embodiments, the milk fraction which is used as a starting material for hydrolysis comprises one or more of the caseinoglycomacropeptide component present in milk, proteose peptones, α-lactalbumin, β-lactoglobulin, serum albumin, and the immunoglobulin fraction present in milk. There are also many other proteins in WPI which are present in small amounts and which have not yet been clearly identified or quantitated.

Other milk fractions which contain a proportion of the proteins found in whey may also possess the desired biological activity described herein. The skilled addressee would be readily able to determine whether any particular milk fraction possesses the desired activity on hydrolysis by using the in vitro and in vivo methods described in the Examples.

The biological activity demonstrated in hydrolysed WPI is able to survive the conditions involved in WPI production, such as anion exchange, diafiltration and spray drying.

In addition, the biological activity demonstrated in hydrolysed WPI is able to survive the conditions involved in specific enzyme digestion and enzyme inactivation involved in the hydrolysis process. Accordingly, any or all of these steps could also be used in the preparation of a milk fraction and be expected to retain the desired biological activity. The biological activity which is present in the WPI is also able to survive the process of pasteurisation, as the material which is present in WPI is pasteurised as milk and as whey during WPI manufacture.

Although the present examples utilise whey protein from bovine milk, due to the relatively similar formulation of milk possessed by domestic species it is anticipated that milk from other animals including sheep, goats, horses and buffalo will also provide a suitable source of starting material. There may also be advantages in using whey protein of human origin, for instance in the preparation of formulations for administration to newborn babies.

As used herein, the term "hydrolysis" refers to the breakdown of proteins or polypeptides into shorter polypeptides, and oligopeptides and possibly, to a small extent, component amino acids.

Hydrolysis may be carried out by chemical means, for instance using acid, or by enzyme treatment. Hydrolysis by a chemical treatment, such as acid hydrolysis, may be a method of producing a hydrolysate, provided that the desired biological activity is retained.

The conditions of hydrolysis may be controlled such that the resultant hydrolysate possesses an enhanced activity in inhibiting the expression of TNFα (using the in vitro methods as described in the examples below) and/or in increasing the muscle force generating capacity (using the in vivo methods described in the examples below) when compared to the starting material before hydrolysis.

The conditions which are likely to influence the relative activity of the hydrolysate when compared to the starting material include the incubation and enzyme inactivation temperatures, the pH of the reaction and inactivation, the length of time of hydrolysis and the type of enzyme used.

In a particular embodiment, the hydrolysis is an enzyme hydrolysis. Preferred enzymes are proteinases of microbial origin, in particular either bacterial origin or fungal origin. It may be advantageous for the enzyme to be a metalloproteinase, both in terms of the substrate specificity and the ability to inactivate the enzyme by controlling the availability of the essential metal ion.

It may be advantageous to utilise proteinases which possess proteinase activity at close to neutral pH, in particular from pH 5.3 to 8.5.

The hydrolysis of WPI as exemplified in the present specification was carried out using proteinase enzyme activity found in the commercial preparation "Neutrase®" (Novozymes). This product contains a neutral proteinase component produced by submerged fermentation of selected strain of *Bacillus amyloliquefaciens*. The protease is a metallo (Zn) endoproteinase which is capable of the moderate to extensive breakdown of most proteins to smaller peptides.

It is anticipated that other proteinases which are capable of hydrolysis of WPI or other milk fractions will also generate the enhanced biological activity identified by the inventors.

Metalloproteinases from the IUBMB Enzyme Nomenclature class EC 3.4.24.28 (also known as bacillolysins, *Bacillus* metalloendopeptidase; *Bacillus subtilis* neutral proteinase; anilozyme P 10; *Bacillus* metalloproteinase; *Bacillus* neutral proteinase; megateriopeptidase) are understood to possess similar proteolytic activity to Neutrase®, and any one or more are contemplated for use in the hydrolysis. For example, the neutral metalloproteinases of bacterial origin "Protease N 'Amano'" (Amano Enzyme, Inc.) and "Corolase N" (AB Enzymes) which are also a member of this enzyme class have been demonstrated by the inventors to produce similar enhanced anti-inflammatory effects in vitro to the use of Neutrase®, and accordingly hydrolysates produced using these enzymes are anticipated to also possess the enhanced in vivo biological activities exhibited by hydrolysates produced with Neutrase®.

Similarly, enzymes from the IUBMB Enzyme Nomenclature class EC 3.4.21.62 (also known as subtilisin, Alcalase®; alcalase 0.6L; alcalase 2.5L; colorase N, ALK-enzyme; bacillopeptidase A; bacillopeptidase B; *Bacillus subtilis* alkaline proteinase bioprase; bioprase AL 15; bioprase APL 30; colistinase; subtilisin J; subtilisin S41; subtilisin Sendai; subtilisin GX; subtilisin E; subtilisin BL; subtilisin A (Type VIII); genenase I; esperase; maxatase; thermoase PC 10; protease XXVII; thermoase; superase; subtilisin DY; subtilopeptidase; SP 266; savinase 8.0L; savinase 4.0T; kazusase; protease VIII; optimase; opticlean; *Bacillus subtilis* alkaline proteinase; protein A 3L; savinase; savinase 16.0L; savinase 32.0 L EX; orientase 10B; protease S and similar serine endopeptidases are candidate enzymes which are potentially suitable for hydrolysis. The use of Alcalase® from this class has been demonstrated by the inventors to produce similar anti-inflammatory effects in vitro to the use of Neutrase®, and accordingly hydrolysates produced using one or more enzymes from this class are anticipated to also possess the in vivo biological activities exhibited by hydrolysates produced with Neutrase®.

Whether a particular enzyme from IUBMB Enzyme Nomenclature class EC 3.4.24.28 or EC 3.4.21.62 is able to produce the enhanced desired biological activity may be readily determined using the in vitro methods described herein in Example 3 and/or the in vivo methods described in Example 4.

The enhanced biological activity which has been identified by the inventors does not appear to follow from all forms of enzyme hydrolysis of whey proteins, as the enhanced biological activity is not exhibited in vitro following hydrolysis of WPI with trypsin, trypsin and Debitrase DBP20, and trypsin and Corolase LAP. Accordingly, in one embodiment the hydrolysate is not produced by trypsin digestion. In other embodiments, the hydrolysate is not produced by any one or more of Multifect P3000, S Amano, P Amano 6, Savorase MFF, Debitrase HWY20, A Amano 2, Flavourzyme 500L, Protamex, Corolase® LAP, Debitrase DBP20, Bioprotease N100L, M Amano, Peptidase R, P Amano 6 and Debitrase DBP20, P Amano 6 and Corolase LAP, A Amano 2 and Debitrase DBP20, A Amano 2 and Corolase LAP, S Amano and Debitrase DBP20, S Amano and Corolase LAP, Multifect P3000 and Debitrase DBP20, or Multifect P3000 and Corolase LAP.

There are a number of desirable properties that may be possessed by an enzyme which is to be used. It is desirable that the protease for hydrolysis is non-toxic over a broad range of concentrations. Preferably the enzyme is tolerated when ingested by a subject. It may be advantageous if the enzyme can be readily inactivated by conditions which do not inactivate the desired biological activity present in the hydrolysate, for example by mild heating, and/or that it can be readily separated from the hydrolysate, for instance by immobilisation of the enzyme to a solid support or by ultrafiltration to retain the enzyme while allowing the active component of the hydrolysate to pass through and be collected. There may be advantages in manufacturing of a hydrolysate if the enzyme can be provided to the starting material at a high specific activity. It may be advantageous if the enzyme is not inactivated by physical conditions such as pH and ionic formulation of the milk or milk fraction, or inactivated by components found in milk fractions or whole milk. In particular embodiments the enzyme will possesses proteinase activity at a pH close to neutral, in particular embodiments an optimal enzyme activity which lies within the range of pH 5.5 to 8.5, and more particularly 6.3 to 8.0.

Methods for enzymic hydrolysis of whey proteins and techniques for controlling these reactions are described in detail, for example, in U.S. patent application Ser. No. 11/083,662 (US patent application publication 2005/0164340), the entire contents of which is incorporated herein by cross-reference. The degree of hydrolysis of the starting material may also contribute to the activity of the hydrolysate which is produced. The degree of hydrolysis of both the starting and hydrolysed materials may be determined by the OPA methodology (Lee K S, Drescher D G., Fluorometric amino-acid analysis with o-phthaldialdehyde (OPA), Int. J. Biochem. 1978; 9 (7): 457-467), the entire contents of which is incorporated herein by cross reference.

The hydrolysis conditions exemplified herein were relatively mild, and consequently it is anticipated that complete hydrolysis of the starting material is not required for the enhancement of biological activity. Accordingly, the term "hydrolysis" is intended to encompass at least partial hydrolysis of the whey protein. Whey protein hydrolysates having a degree of hydrolysis of about 0.5% to about 20% contain less than about 5% of free amino acids, about 15% to about 55% of peptides having a molecular weight of less than 1000 Da, about 20% to about 55% of peptides having a molecular weight of 1000 Da to 5000 Da, and about 15% to about 35% of peptides having a molecular weight of greater than 5000 Da. In one embodiment the net degree of hydrolysis (%) is between 0.5% and 10%, and more preferably 0.5% and 4%.

The term "hydrolysate" refers to the mixture of intact proteins or polypeptides, shorter polypeptides, and oligopeptides and component amino acids which is produced by hydrolysis.

It is well recognized that eccentric exercise induces muscle damage and inflammation. This muscle damage can be readily identified by comparing the force generating capacity (torque) of the injured muscle with the muscle pre-injury. Using the methods described in the examples below, muscle torque normally does not recover to pre-injury levels for up to seven days post injury. The present inventors have demonstrated that orally-administered hydrolysates produced from whey protein dramatically attenuate the loss of muscle torque which follows muscle damage induced by repetitive maximal exertion, allowing a dramatically hastened recovery to normal peak isometric torque levels, in the present example within 24 hours after muscle injury. In addition, the administered hydrolysates improved the force generating capacity of the muscle tissue over the pre-injury baseline level within 24 hours following exercise. This increase in muscle torque was not demonstrated in subjects administered placebo or non-hydrolysed WPI.

As the loss of muscle function can be triggered by a variety of injurious stimuli, it is also contemplated that the hydrolysates may also attenuate loss of muscle force generation capacity which arises from a variety of sources of muscle damage, such as bruising and/or trauma.

This activity may be associated with the ability of WPI and, to a greater degree, WPI hydrolysates to down-regulate the production of TNFα in vitro as demonstrated in macrophage cultures described below. Based on previous studies by the present inventors on milk fractions, the in vitro results may be predictive of the activity of hydrolysates in down-regulating one or more inflammatory markers in muscle which arise following exercise-induced damage. Accordingly, it is anticipated that the WPI and WPI hydrolysates may possess activity in attenuating inflammation arising from muscle damage, such as the up-regulation of jun-B and c-fos gene expression in injured muscle tissue.

In addition, the in vitro assay of TNFα gene expression in macrophages may be conveniently used to monitor the production of hydrolysates in order to maximise their biological activity.

Accordingly, the term "desired biological activity" as used herein refers to any one or more of the attenuation of loss of muscle force generating capacity following muscle damage in a subject, the increase of muscle force generating capacity over baseline levels, the down-regulation of TNFα expression in macrophages in an in vitro assay described herein and the attenuation of expression of inflammation markers in muscle following muscle damage, such as exercise induced muscle damage. The attenuation of loss of muscle force generating capacity may include a reduction in the loss in torque exhibited following injury and/or the hastening the recovery of torque to pre-injury levels.

Without wishing to be bound by any proposed mechanism, preliminary in vitro results suggest that WPI and hydrolysates of WPI, such as those produced with Neutrase® or Alcalase®, may stimulate growth of fibroblast cells, suggesting that the hydrolysates may stimulate muscle growth or repair, and suggesting that the hydrolysates may have muscle repair or building applications beyond that possessed by non-hydrolysed WPI.

Hydrolysates were demonstrated to be effective in attenuating loss of muscle function and in improving the force generation capacity of muscle when administered to subjects immediately after muscle injury-inducing exercise. The peak isometric and eccentric torque results also suggest that the further administration of hydrolysate at 6 and 22 hours after exercise-induced muscle damage maintained the improvement in muscle force generation capacity for at least 24 hours following muscle damage. Accordingly, it is anticipated that while the hydrolysates may be administered after exercise, as demonstrated herein, or for periods longer than 24 hours after exercise, they may be additionally or alternatively administered before exercise. Thus it is contemplated that the hydrolysates may be used prophylactically, for instance in circumstances where it is anticipated that strenuous exercise may result in muscle damage, or therapeutically after exercise in order to attenuate the muscle responses arising from damage.

The present inventors have demonstrated that the orally administered hydrolysates, unlike non-hydrolysed WPI, were able to induce an increase in muscle force generating capacity over baseline (pre-injury) levels 24 hours after exercise. It is contemplated that that the hydrolysates may be administered regularly or intermittently over an extended period, preferably in combination with regular or intermittent exercise, in order to stimulate increased muscle force generation capacity. Such a use is also contemplated in subjects wishing to build muscle strength or in subjects predisposed or at risk of muscle wasting, such as the elderly or the infirm.

Because the whey proteins and hydrolysates are derived from well-characterised milk products such as whey which are known to be suitable as dietary supplements, they may be advantageously administered as nutraceutical formulations. The present inventors have demonstrated that hydrolysates of whey protein in the form of a WPI hydrolysate is well tolerated and palatable when admixed with sweeteners and administered to subjects in liquid form.

It is anticipated that the hydrolysates may be administered as a nutraceutical formulation. A "nutraceutical" as defined herein represents an edible product isolated or purified from food, in this case from milk, which is demonstrated to have a physiological benefit or to provide protection or attenuation of an acute or chronic disease or injury when orally administered. The nutraceutical may thus be presented in the form of a dietary supplement, either alone or admixed with edible foods or drinks.

The nutraceutical formulation may be in any suitable form. For example, the nutritional formulation may be in the form of a soluble powder, a liquid or a ready-to-drink formulation. Alternatively, the nutritional formulation may be in solid form; for example in the form of a ready-to-eat bar or breakfast cereal. Various flavours, fibres, sweeteners, and other additives may also be present.

The formulation may be fed to a patient via a nasogastric tube, jejunum tube, or by having the patient drink or eat it.

The nutraceutical formulation may be produced as is conventional; for example, the formulation may be prepared by blending together the whey protein or hydrolysate and other additives. If used, the emulsifiers may be included in the blend. Additional vitamins and minerals may be added at this point but are usually added later to avoid thermal degradation.

If it is desired to produce a powdered nutraceutical formulation, the whey protein or hydrolysate may be admixed with additional components in powdered form. The powder should have a moisture content of less than about 5% by weight. Water, preferably water which has been subjected to reverse osmosis, may then be mixed in to form a liquid mixture.

If the nutraceutical formulation is to be provided in a ready to consume liquid form, it may be heated in order to reduce the bacterial load. If it is desired to produce a liquid nutraceutical formulation, the liquid mixture is preferably aseptically filled into suitable containers. Aseptic filling of the containers may be carried out using techniques commonly available in the art. Suitable apparatus for carrying out aseptic filling of this nature is commercially available.

It will be appreciated that the optimal dosage of the whey protein or the hydrolysate which is administered will depend on the subject and the application which is desired. It is anticipated that a subject would be administered the formulation in an amount sufficient to deliver at least 50 to 1500 mg of hydrolysate protein per kg body mass per day, and in some embodiments 50 to 1100 mg of hydrolysate protein per kg body mass per day and in particular embodiments 50 to 600 mg of hydrolysate protein per kg body mass per day. The formulation may be taken in multiple dosages over the day in order to deliver this amount to the subject.

In a particular embodiment the dose provides 50 to 1500 mg/kg of WPI or hydrolysate. In a particular embodiment adult men are provided with a dose of roughly 50, 350, 570, 1100 or 1500 mg of hydrolysate protein per kg body mass per day for an average 70 kg individual, preferably in a daily dose. Such a dose may be provided by 4, 25, 40, 75 or 100 g of WPI or hydrolysate powder.

The formulation may be administered in one dose or in 2-3 divided doses. In a preferred embodiment the formulation is administered immediately after exercise or within 20 minutes to 2 hours of exercise.

It should be clearly understood that while the exemplification provided herein is limited to administration of a nutraceutical to human subjects, the same or similar formulations could also be administered to non-human mammals in which similar beneficial physiological responses are desired. It is clearly desirable, for instance to minimise adverse responses to muscle damage and increase muscle force generating capacity in mammals in which speed or optimal muscle strength is desired, for example in racehorses or greyhounds, or to optimise muscle mass in livestock used for meat production, such as cattle, pigs, and sheep.

In the present specification, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

As used in the present specification, except where the context requires otherwise due to express language or necessary implication, the term "consisting essentially of" is intended to convey that additional elements may be added but that these additional elements do not materially affect the basic and novel characteristic of the stated feature or features. Examples of additional elements which do not materially affect the basic and novel characteristic of WPI or a hydrolysate of WPI include but are not limited to flavouring agents, sweeteners, preservatives, solvents and diluents.

As used in the present specification, the singular forms "a", "an" and "the" include plural aspects unless the context clearly dictates otherwise. Thus, for example, reference to a whey protein includes one or more whey proteins.

The invention will now be described by reference to the following non-limiting examples.

Example 1. Preparation of Whey Protein Isolate

The aim of the WPI process is to enrich whey proteins by removing other whey components, such as water, lactose, fat, and ash (which comprises the mineral component of milk such as phosphorous, sodium, potassium, calcium, magnesium, and other metals), until the remaining material is greater than 90% whey proteins (sample basis). Processes which are commonly used commercially to produce WPI comprises steps of anion exchange chromatographic separation, ultrafiltration (UF) and spray drying.

The WPI process works on the principle of anion exchange chromatography, with a large diameter resin which allows for a high flow rates with viscous materials. The starting material may be sweet whey produced by rennet coagulation or acid whey which results from the removal of casein by adding an acid. It is anticipated that whey produced by other methods, such as ultracentrifugation, microfiltration or ethanol precipitation would also be suitable. Ideally the starting material for WPI production is WPC35 (whey protein concentrate 35% w protein/w solids), which is a generic product produced by the ultrafiltration of raw whey to remove ash and lactose. This process is widely known to those in the dairy industry. A very similar product is also produced by using skim milk instead of whey.

The starting material is introduced onto anion exchange columns (GibcoCel CR201) to load the resin with predominantly negatively charged (at the pH of whey of 6.5) whey components. The columns are rinsed with water to remove unbound materials, and the bound whey components are eluted and the columns regenerated with a mixture containing 0.75 M sodium chloride and 0.75 M potassium chloride, after which the columns are rinsed to remove residual chloride.

The whey components eluted from the CSEP are desalted and concentrated by diafiltration through low temperature, low molecular weight, spiral ultrafiltration membranes. This step retains proteins, but removes salt, ash components and lactose. During this step total solids rise from 4% to 25% and the protein concentration rises from 50% of total solids to greater than 90% of total solids.

The purpose of the dryer is to remove the majority of the remaining water in the product until a maximum of 5% water remains. The dryer does this by atomizing the WPI concentrate in a chamber filled with hot air. As the resultant WPI powder is subsequently reconstituted in water as it is prepared for the hydrolysis, it may be possible to eliminate the drying step from this process.

The inventors have examined hydrolysates of WPI produced from cheese whey and from acid whey. Both contain similar bioactivity on enzyme digestion, and so it is anticipated that the type of WPI will not materially alter the resultant biological activity produced by the WPI hydrolysate.

WPI from each of sweet whey and acid whey WPI were used for the manufacture of the hydrolysates tested in vitro, but only sweet whey WPI hydrolysates were tested in vivo. The hydrolysates produced from sweet whey WPI and from acid whey WPI demonstrated very little difference in the in vitro assays, and therefore it is expected that the results for sweet whey WPI hydrolysates in vivo may be extended to acid whey hydrolysates.

Example 2. Hydrolysis of WPI

The protease solution used in this example is a commercial product "Neutrase"® (Novozymes).

The target pH for the hydrolysis reaction was pH 6.5. The pH change during hydrolysis was limited, so it was practical to commence hydrolysis at pH 6.6 and not readjust the pH during the reaction. The final pH was around 6.4.

Three kilograms of WPI as prepared according to Example 1 was reconstituted in 27 l water to make up 30 l 10% (w/v) solids solution. The pH was adjusted to 6.6 with 4M NaOH prior to heating to 50° C.

Once heating had commenced, the solution was stirred continuously.

4.5 g of Neutrase® 1.5MG (Novozyme) was dissolved in 45 ml water to prepare a 10% solution, which was then added to the WPI solution. The pH was continually monitored and adjusted only if pH fell below 6.4. The hydrolysis process can be monitored in real time by the decrease in pH. The actual amount of hydrolysis that has taken place can be determined afterwards by measuring the "degree of hydrolysis" using a method based on o-phthalaldehyde (for example Lee et al., 1978; supra). The actual amount of hydrolysis taking place under the conditions described above is not very high, with an observed net degree of hydrolysis (%) between 0.3 and 3.0.

After 60 min hydrolysis the solution was adjusted to pH 4.0 with 4M HCl and the temperature maintained at 50° C. for 30 min to deactivate the Neutrase®. The resulting hydrolysate was cooled to 25° C. and the pH readjusted ≥pH 6.5, and ideally to pH 7.0.

The hydrolysate was then dried, ideally by freeze-drying at 35° C.

Hydrolysates of WPI or other milk fractions which contain whey protein are produced using other proteinase enzymes, and their activity in inhibiting the expression of TNFα in macrophages or stimulating fibroblast cell growth in the in vitro methods described herein in Example 3 is screened. These hydrolysates are also screened for their activity in attenuating symptoms of muscle damage and in enhancing muscle contractile force in subjects using the methods described below.

Example 3. Modulation of the Expression of TNFα in Macrophages and Stimulation of Fibroblast Cell Division In Vitro TNFα Release RAW264.7 macrophages were seeded into 96-well plates at a density of $2 \times 10^4$ cells/well in DMEM culture medium containing 10% heat-inactivated fetal bovine serum (FBS). Cells were then maintained in culture for 48 h at 37° C. Upon reaching the optimal cell density, the serum-containing medium was removed and cells stimulated under serum-free conditions for 6 h at 37° C. with 50 ng/ml bacterial lipopolysaccharide (*Escherichia coli* 055:B5) in the presence of either vehicle control (0.9% saline) or test dairy sample at 2 mg/ml. All samples contained sweetener and flavouring agent; the placebo sample contained no other compounds, the WPI sample contained WPI obtained according to the method described in Example 1, the hydrolysed WPI samples were taken from two different Neutrase® hydrolysis batches produced according to the method described in Example 2, and the casein sample contained commercially available casein (acid casein, Murray Goulburn Co-Operative).

Following the 6 h stimulation period, levels of TNFα present in the cell-conditioned medium were measured using a highly specific TNFα sandwich ELISA and data expressed as % inhibition of TNFα release (relative to cells pre-treated with vehicle alone). Cell viability was assessed by alamarBlue staining.

Fibroblast Growth

BalbC3T3 fibroblasts were seeded into 96-well plates at a density of $0.8 \times 10^4$ cells/well in DMEM culture medium containing 10% fetal bovine serum (FBS) and maintained in culture overnight at 37° C. Following the overnight culture, the serum-containing medium was removed and cells stimulated in serum-free DMEM medium containing either vehicle control (0.9% saline) or test sample at 2 mg/ml. All test samples contained sweetener and flavouring agent; the placebo sample contained no other compounds, the WPI sample contained WPI produced according to the method of Example 1 and the hydrolysed WPI samples were taken from two different batches of Neutrase® hydrolysis of WPI according to the method of Example 2.

Cells were maintained in culture for an additional 48 h, after which time the culture medium was aspirated and cell growth quantitated by alamarBlue staining. Data was expressed as % growth (above cells treated with vehicle control).

Figure 4:
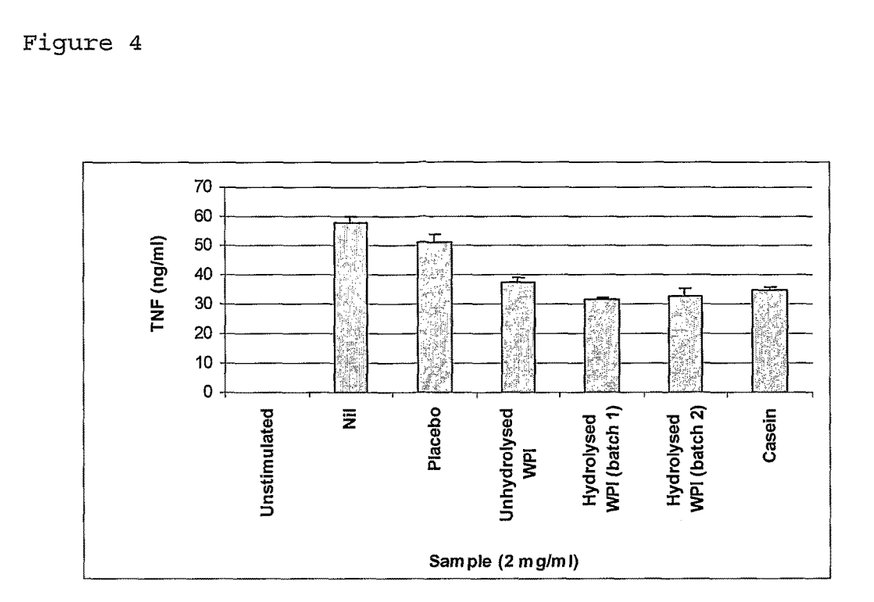
FIG. 4 provides in graphical form the results of in vitro testing of test samples for their ability to influence the expression of the pro-inflammatory cytokine TNFα in a LPS stimulated macrophage cell line.
Figure 5:
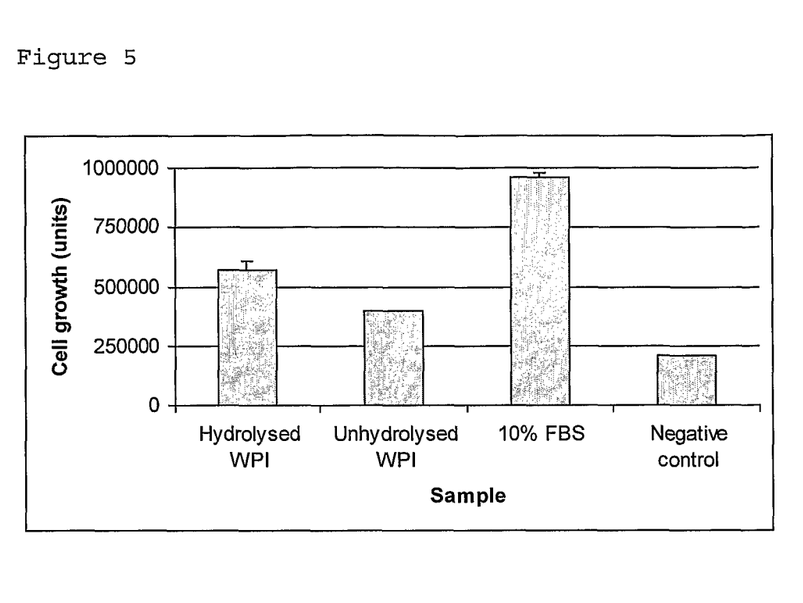
FIG. 5 provides in graphical form the results of in vitro testing of test samples for their ability to influence fibroblast cell proliferation. "FBS" represents fetal bovine serum.

The results of these experiments are presented in FIGS. 4 and 5.

Of all the samples tested, the Neutrase® hydrolysed WPI possessed the greatest activity both in inhibiting the expression of TNFα by LPS stimulated macrophages and in stimulating the growth of fibroblasts.

Example 4. The Modulation of Exercise Induced Muscle Damage

The study described below used a randomised, double-blind, placebo-controlled parallel design. Assessments of the strength, power and local muscular endurance of the quadriceps muscles of the right leg, as well as muscle soreness and blood markers of inflammation, were assessed prior to the induction of muscle damage which was induced through the performance of maximal eccentric exercise, immediately after the induction of muscle damage, and 1, 2, 6 and 24 hours after.

Immediately following the induction of muscle damage, subjects were randomly allocated to consume 250 ml of flavoured and sweetened water (control) or 250 ml of flavoured and sweetened water containing 25 g of Neutrase®-treated WPI (as prepared according to Example 2), 25 g of WPI (as prepared according to Example 1) or 25 g of casein (acid casein, Murray Goulburn Co-operative Ltd). These test samples were consumed immediately after assessments of muscle function and inflammation which immediately followed the induction of muscle damage, and again after the assessments at 6 hours and then at 22 hours (i.e. 2 hours prior to the final assessments).

Figure 1:
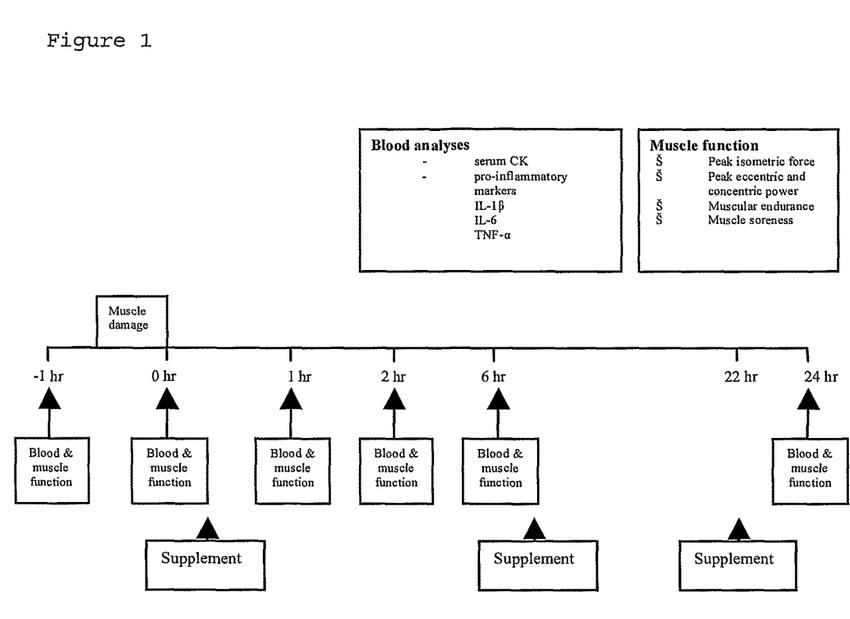

Dietary intakes during the 24 hr preceding testing and during the 24 hr intervention period were assessed using diet diaries. FIG. 1 below indicates the experimental design. Subjects were excluded from participation if they:
- participated in regular physical activity more than once per week for the purpose of improving or maintaining their physical fitness.
- had undertaken resistance training of the quadriceps muscles during the three months prior to their anticipated participation in this study.
- had a knee, quadricep or other musculo-skeletal or medical problem which might have interfered with their ability to perform the required exercise to induce muscle soreness.
- had experienced significant delayed onset muscle soreness (DOMS) in their quadriceps muscles during the three months prior to their anticipated participation in this study.
- had had any previous allergic or sensitivity response to dairy proteins Subjects were instructed not to take over-the-counter medication, "cold & flu" treatments, analgesics, aspirin or other anti-inflammatory preparations for at least 7 days prior to the study period, and to abstain from alcoholic beverages for 48 hours prior to or during the study period.

Muscle damage was induced through the performance of 100 maximal voluntary eccentric isokinetic contractions of the quadriceps muscles of the right leg on a Kin-Com isokinetic dynamometer (Chattecx, TN, USA). In order to induce DOMS, each subject performed 10 warm-up repetitions at low resistance, followed by 100 maximal voluntary eccentric muscle contractions of the knee extensors at an angular velocity of 40°/sec through an 80° range of motion. Subjects performed a maximal isometric contraction against the dynamometer lever arm for approximately 1 sec before the initiation of each eccentric contraction, and with continued maximum effort, resisted the forced lengthening of their knee extensors. The knee extensors were relaxed at the end of the eccentric contraction, and during the recovery phase the relaxed leg was returned to the starting position by the experimenter. Body position, approximate axis of rotation of the knee joint and dynamometer lever arm length were consistent for each subject, and verbal encouragement was given during all contractions.

The degree of muscle soreness was evaluated using a 100 mm visual analogue scale (VAS) using published techniques (Huskinsson, E., Visual analogue scales, in Pain measurement and assessment, R. Melzack, Editor. 1983, Raven Press: New York. p. 33-37) immediately prior to inducing muscle damage and again immediately following the completion of the exercise, and 1, 2, 6 and 24 hours post-exercise using the VAS.

The VAS consisted of a 100 mm horizontal line with the ends closed off, and anchor points consisting of "no soreness" on the left to the "worst soreness possible" on the right hand end. Subjects were seated and requested to extend the knee (so the leg was horizontal) in which soreness was being assessed with a 5 kg mass suspended from their ankle. The subjects placed a mark at the point on the VAS corresponding to their perception of the soreness in the quadriceps muscles of that leg. The extent of the muscle soreness was quantified as representing the measured distance (in mm) from the left hand end of the continuum to the mark made by the subject.

The VAS data obtained demonstrated that muscle soreness increased in all groups following eccentric contractions, and remained elevated throughout the study, with no statistically significant differences between groups.

Muscular strength, eccentric and concentric muscle power and muscular endurance of the quadriceps muscles of the right leg was assessed using an Isokinetic dynamometer (Kin-Com 125AP, Chattecx Corporation, Tennessee, USA). Isometric muscle strength was determined from the peak torque achieved from 3 maximal isometric contractions with the knee flexed at 90°. Eccentric muscle torque was determined from the peak torque achieved during 3 maximal eccentric muscle contractions of the knee extensors at an angular velocity of 40°/sec through an 80° range of motion. Concentric muscular power and muscular endurance were assessed from 15 consecutive maximal isokinetic knee extension maneuvers at an angular velocity of 40°/sec through an 80° range of motion.

An assessment of muscle damage and the inflammatory response to exercise was made. Blood samples were collected at baseline, immediately following the completion of the 100 eccentric muscle contractions, and 1, 2, 6 and 24 hr post-exercise for assessment of serum creatine kinase activity, and inflammatory markers. The pre- and post-exercise blood samples were placed into serum tubes for Creatine kinase assays or EDTA tubes for assays of inflammatory markers. The samples were then spun in a centrifuge and the serum and plasma stored at −80° C. until analysis.

Creatine kinase activity has been shown to increase 24 to 48 hr after the performance of eccentric exercise and is routinely used as a marker of muscle damage following eccentric exercise.

The plasma concentrations of a number of pro-inflammatory cytokines which have been shown to be elevated in response to eccentric exercise will be measured. Tumor necrosis factor α (TNFα) has been shown to reach peak values at the end of exercise, with interleukin (IL)-1β (IL-1β) and IL-6 being increased up to 24 hr post-exercise.

The blood samples are being analyzed using commercial kits for each of these cytokines.

Subjects in the double blind study were randomly allocated to one of 4 groups described above. Each group consumed the same test sample throughout the study. The supplements were provided in pre-weighed sachets containing the supplement and sweetener and were added to water and mixed thoroughly prior to their consumption. The supplement sachets were labelled A, B, C and D and the investigators were blinded to the code during the study and the subsequent analysis of the results. Supplement A was the placebo, B the WPI hydrolysate supplement, C the WPI supplement and D the casein-containing supplement.

The test samples were consumed immediately after the muscle function testing and blood sampling that followed the induction of muscle damage using eccentric exercise and again at 6 hr, then again at 22 hr (i.e. 2 hr prior to the final assessments).

Food eaten during the 24 hour period prior to testing and during the 24 hour intervention period was recorded in a diet diary for subsequent analysis using Foodworks (Xyris software, Brisbane) and the Australian Nutrient database (NUT-TAB).

Baseline parameters for the four supplement groups were compared using one-way analysis of variance (ANOVA). The effect of the different treatments on peak isometric torque and peak eccentric torque over time were compared using repeated measures ANOVA. Where ANOVA demonstrated a significant main effect, post-hoc analysis was completed to determine differences between means using a test of least significant differences. Statistical significance was set at an α-level of $P<0.05$. All data are shown as the mean±SEM.

Results—Peak Isometric Torque

Figure 2:
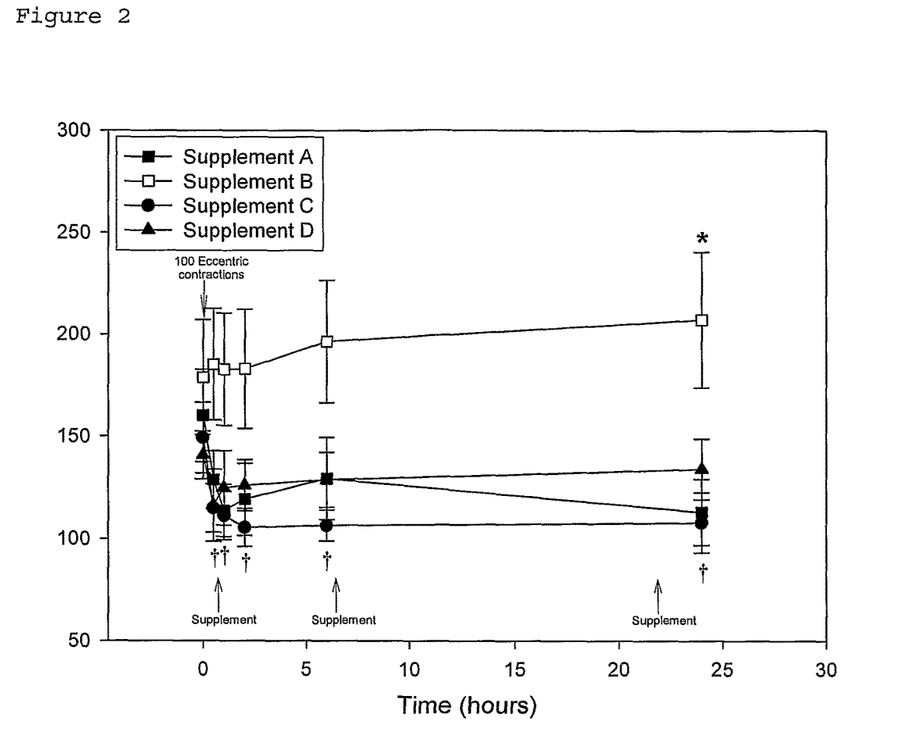

Peak isometric torque results are shown in FIG. 2. Peak isometric torque was not different between groups at baseline. ANOVA indicated that there was a significant effect for time of measurement ($P<0.001$) and an interaction between treatment and time ($P<0.01$), but no significant effect of treatment ($P=0.06$). Post-hoc analysis indicated that this interaction effect was due to a significant increase in torque in subjects taking the WPI hydrolysate test sample, such that torque was significantly higher than baseline by 24 hr ($P=0.03$), no change in torque in subjects taking the casein test sample ($P>0.12$), and significant reductions in torque in subjects taking the placebo and WPI test samples ($P<0.05$). However, while there was no significant reduction in torque in subjects consuming the casein test sample, this response was not significantly different from the responses in subjects who had consumed the placebo or WPI. The increase in torque in subjects who consumed the WPI hydrolysate by 24 hours represented a 14.4±8.9% increase from baseline, which contrasted with a 4.3±7.6% reduction in subjects taking the casein test sample (not a significant reduction), and 31.0±3.0% and 21.3±8.8% reductions in subjects taking placebo and WPI respectively.

Results—Peak Eccentric Torque

Figure 3:
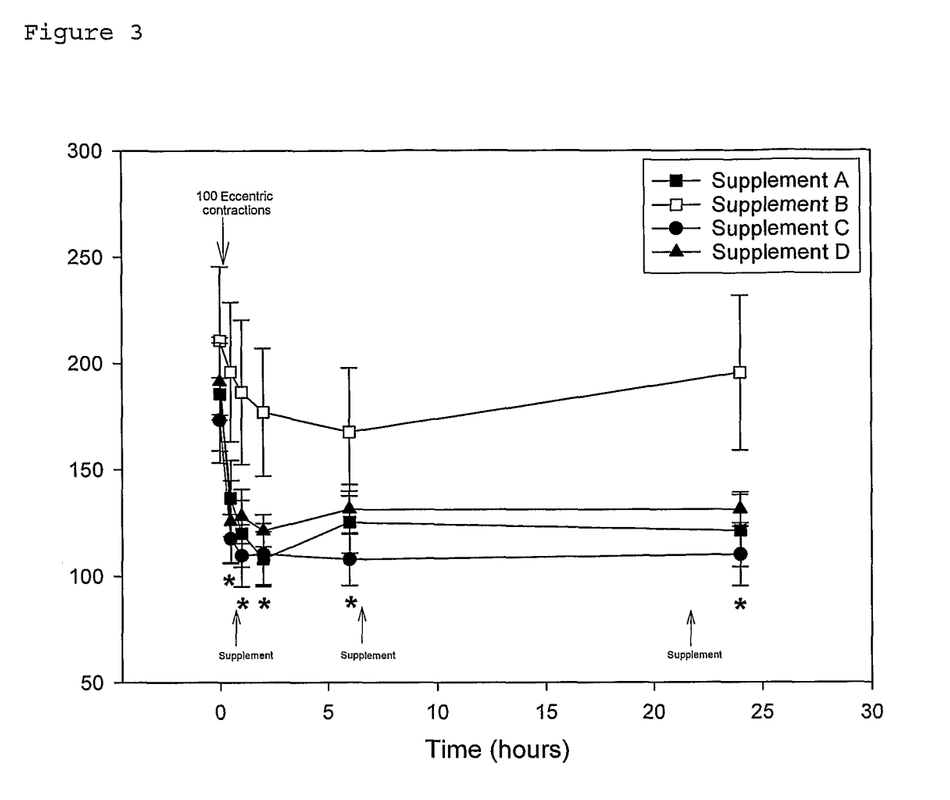
FIG. 3 provides in graphical form the results of the muscle peak eccentric torque testing described in Example 4. "A" represents a placebo supplement, "B" represents the WPI hydrolysate supplement, "C" represents the WPI supplement and "D" represents Casein-containing supplement. Peak eccentric torque assessed at baseline (0 hours), immediately after 100 maximal eccentric contractions, and at 1, 2, 6 and 24 hours after.
* significantly different from baseline (P<0.001).

Peak eccentric torque results are shown in FIG. 3. Peak eccentric torque was not different between groups at baseline. ANOVA indicated no significant treatment ($P=0.26$) or interaction ($P=0.79$) effects, but there was a significant time effect as a result of an overall reduction in torque across all treatment groups immediately after exercise, and torque remained lower than baseline for the duration of the 24 hour study period ($P<0.001$).

The between subject variability in peak eccentric torque in subjects consuming the WPI hydrolysate test sample was approximately double that of the other groups, so in an effort to reduce this variability the data were expressed in terms of the percentage change in peak eccentric force relative to baseline. Using this analysis, ANOVA indicated that there was no significant interaction effect (treatment×time, $P=0.97$), but there was a statistically significant time effect ($P=0.001$) due to torque decreasing for the first hour after completing the 100 maximal eccentric contractions of the quadriceps muscles ($P<0.001$) and then remaining suppressed for the duration of the 24 hour study period. Importantly however, there was a trend toward a treatment effect for the percentage reduction in torque ($P=0.17$) due to a lesser reduction in torque in subjects who had consumed the WPI hydrolysate.

This analysis of the data indicates that WPI hydrolysate not only protected against the attenuation of peak isometric and eccentric torque that occurred following the performance of repeated maximal eccentric muscle contractions, but significantly increased the isometric force generating capacity of the quadriceps muscles compared with the other 3 test samples.

Muscle soreness increased in all groups, and there was no statistically difference in muscle soreness between groups. While data on markers of muscle damage and inflammation are not currently available, it is recognized that eccentric exercise induces muscle damage and inflammation, leading to a loss of force generating capacity of muscle tissue. The attenuation of the loss of force generating capacity in subjects who consumed hydrolysed WPI, and the increase in peak isometric force of ~14% above baseline, indicates that this particular test sample not only reduced the impact of any damage sustained by the muscle on its contractile function, but also improved the force generating capacity of the muscle tissue.

Although the precise mechanism underlying the increase in force generating capacity in these subjects has not been clearly identified, the ability of muscle to generate force is known to be mediated by neural mechanisms, which regulate motor unit recruitment, and by contractile protein content. Data from a previous studies tends to suggest that the improvements in muscle function that were observed in the present study are more likely to be mediated by an increase in contractile protein content, combined with reduced inflammation, than any neural effect.

Example 5. Modulation of Expression of Muscle Inflammation Markers

Subjects arrive at the laboratory in the fasted state and undergo a resting muscle biopsy from the vastus lateralis muscle.

Following the resting biopsy, subjects complete a bout of heavy resistance exercise consisting of 3 sets of 12 repetitions of maximal leg extension exercise. Immediately following the exercise subjects are randomly assigned to receive a test sample as described in Example 4. Both subjects and testers are blinded to the supplementation received.

Further muscle samples are collected 2 and 4 after exercise. Following the third biopsy, subjects ingest a second supplement identical to their first.

24 hours following the exercise, subjects again return to the laboratory in the fasted state for a fourth and final muscle biopsy.

RNA is extracted from the muscle biopsies collected and analysed for changes in the expression of markers of muscle hypertrophy and markers of muscle inflammation.

Two aspects of muscle recovery are investigated, (1) the degree of inflammation evident within the muscle post exercise and (2) the ability of the muscle to adapt by increasing in size (hypertrophy).

c-Fos and JunB collectively make up the transcription factor complex AP-1. The AP-1 complex is important in regulating the genes involved in inflammation following intense or damaging exercise. c-Fos and JunB gene expression is rapidly induced following heavy exercise and provide useful markers of the early inflammatory response within the muscle. c-Fos and JunB expression in muscle biopsies are determined using commercially available kits.

Skeletal muscle hypertrophy is controlled, in part by the activity of the basic-loop-helix family of myogenic regulatory factors (MRFs). The MRF members MyoD and Myogenin have previously been identified as being important in the adaptive response of skeletal muscle to resistance exercise. Another important regulator of muscle growth is myostatin. High levels of myostatin are known to inhibit muscle growth and suppression of myostatin gene expression is evident following heavy resistance exercise. Therefore, MyoD and myogenin and myostatin gene expression are selected as markers of muscle hypertrophy. The expression of these genes is determined using published methods (for instance Megeney et al. (1996). Genes Dev. 10: 1173-1183; Ohkawa et al. The EMBO Journal (2006) 25, 490-501; and Roth et al, Experimental Biology and Medicine 228:706-709 (2003)).

Example 6. Producing Further WPI Hydrolysates

Enzymatic hydrolysis of WPI as produced according to Example 1 was carried out with three examples of each of the two nominated EC classes, to confirm that bioactivity was not specific to the Neutrase® digest made according to Example 2.
Examples of EC 3.4.24.28:
 Neutrase®,
 Protease N "Amano"
 Corolase N
Examples of EC 3.4.21.62:
 Alcalase®,
 Subtilisin A (Type VIII)
 Optimase
Protocol for Manufacture (Laboratory Scale)

At 1600 h WPI produced according to Example 1 was dissolved into water to produce 1 L 10% (w/w) WPI solution. The WPI was stored at 4° C. overnight. On the following day at 1400 h the 1 L bottle containing the WPI was gently heated to 50° C. and the pH adjusted to pH 6.6 by the careful addition of 2M NaOH. The 1 L WPI solution was subdivided into six bottles, each containing 100 mL 10% (w/w) WPI solution.

Approximately 50 mg of an enzyme (Neutrase®, Protease N "Amano", Corolase N, Alcalase®, Subtilisin A [Type VIII] or Optimase) was added to the WPI and the WPI solution was then incubated at 50° C. for 1 h.

The pH was periodically measured, but not adjusted during the 1 h incubation. The remaining enzyme was deactivated by adjusting the hydrolysed WPI solution to pH 4.0 by adding 2M HCl and then incubating at 50° C. for 30 min.

The solution was then neutralised (pH 5.5) by the addition of 2M NaOH. The samples were freeze-dried for 48 h at a vacuum of 1 mBar while being heated at 45° C.

The powders were sent to TGR Biosciences for bioactivity assay as described previously in Example 3, except the samples were assayed at 0.2 mg/ml and 1 mg/ml.

Figure 6:
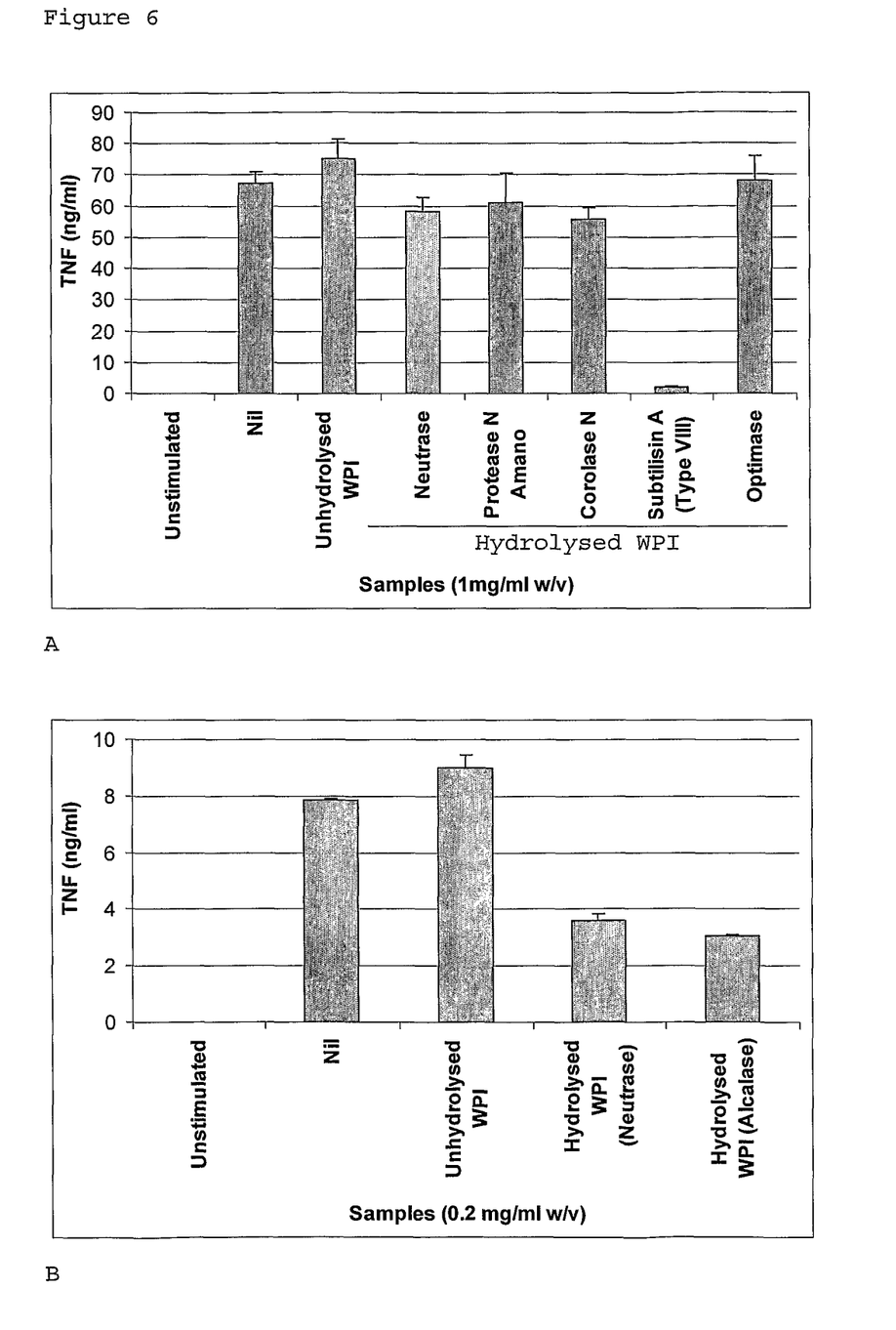
FIG. 6 provides in graphical form the results of in vitro testing of samples for their ability to influence the expression of the pro-inflammatory cytokine TNFα in a LPS stimulated macrophage cell line, A at 1 mg/ml w/v and B at 0.2 mg/ml w/v.

The results are shown in FIG. 6. At 1 mg/ml subtilising A (Type VIII) is by far the best inhibitor of TNFα expression by LPS stimulated macrophages but all the other hydrolysates have better inhibitory activity than unhydrolysed WPI at 0.2 mg/ml and 1.0 mg/ml.

The results confirm the findings of FIG. 4.

Example 7. Modulation of the Expression of TNFα in LPS Stimulated Macrophages—Competitor Controls The experiments carried out in Example 3 were repeated with commercially available milk fraction products as controls to show that the hydrolysates of the present invention act differently to formulations known in the art in relation to TNFα expression.

The samples tested were:

| | | |
|---|---|---|
| A | "iso100" | available from Dymatize (89% protein) |
| B | "Gold standard" | available from Optimum (81.63% protein) |
| C | "HP100" | available from ASN (89% protein) |
| D | "VP2" | available from AST (85.7% protein) |
| E | "Hydroxyphase" | available from Max (90% protein) |
| F | WPI | see Example 1 (89% protein) |
| G | Neutrase digest of WPI as made according to Example 2 (88% protein) | | nWGFE Whey Growth Factor extract made according to PCT/AU2006/001323

Figure 7:
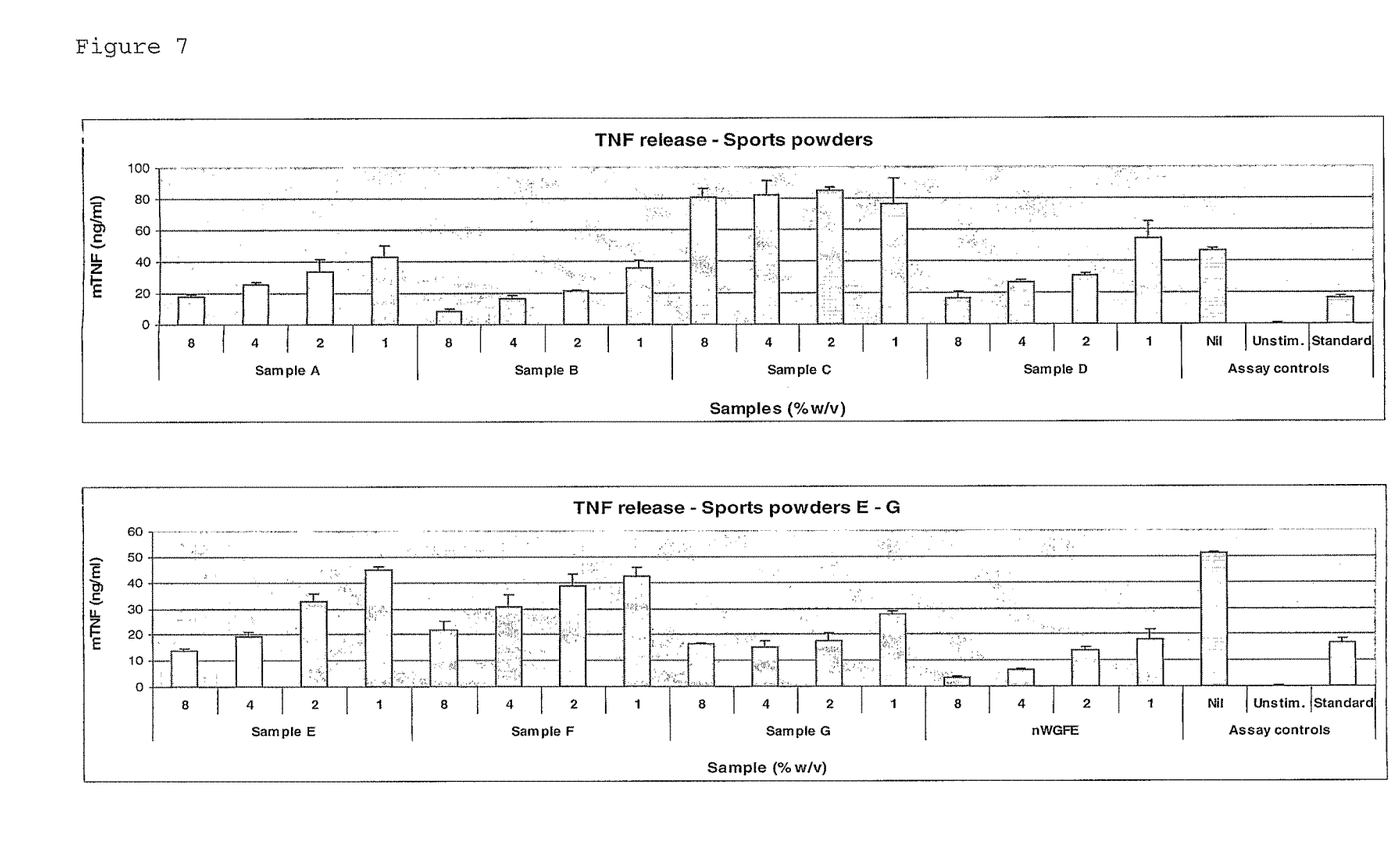
FIG. 7 provides in graphical form the results of in vitro testing of samples for their ability to influence the expression of the pro-inflammatory cytokine TNFα in a LPS stimulated macrophage cell line, at 1, 2, 4 and 8 mg/ml w/v.

The results as shown in FIG. 7 illustrate the capacity of a hydrolysate according to the present invention to inhibit the expression of TNFα from LPS stimulated macrophages as compared to other samples, which in the most part stimulate expression of TNFα.

It will be clearly understood that, although a number of prior art publications are referred to herein, this reference does not constitute an admission that any of these documents forms part of the common general knowledge in the art in any country.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of attenuating a reduction in muscle function which results from muscle damage and/or for enhancing recovery from muscle damage and/or for enhancing the force generating capacity of muscle in a subject in need thereof, the method comprising:
 administering to said subject a formulation comprising a hydrolysate hydrolysate of whey protein having a net degree of hydrolysis between 0.5% and 10% by weight, wherein the hydrolysate is obtained by enzymatic hydrolysis of whey protein with a proteinase selected from the group consisting of a bacillolysin proteinase and a subtilisin proteinase and wherein the formulation is administered in an amount to provide at least 50 mg/kg body weight to 1500 mg/kg body weight of the hydrolysate of whey protein.

2. The method according to claim 1, wherein the muscle damage is exercise-induced muscle damage.

3. The method according to claim 1, wherein the formulation is administered immediately after exercise.

4. The method according to claim 1, wherein the formulation is administered 20 minutes to 2 hours after exercise.

5. The method according to claim 1, wherein the formulation is administered orally.

6. The method according to claim 1, wherein the whey protein is a whey protein isolate or a whey protein concentrate.

7. The method according to claim 1, wherein the hydrolysate has a net degree of hydrolysis in a range of between 0.5% and 4% by weight.

8. The method according to claim 1, wherein the enzyme cleaves peptides after bulky or aromatic residues.

9. The method according to claim 1, wherein the enzyme cleaves peptides at a cleavage site preceded by large uncharged residue.

10. The method of claim 1, wherein the hydrolysate comprises about 15% to 35% of peptides having a molecular weight greater than 5000 Daltons.

11. A method of attenuating a reduction in muscle function which results from muscle damage and/or for enhancing recovery from muscle damage and/or for enhancing the force generating capacity of muscle in a subject in need thereof, the method comprising
administering to said subject a formulation comprising an effective amount of an enzymatic hydrolysate of whey protein having a net degree of hydrolysis of 0.5% and 10% by weight, wherein the hydrolysate is obtained by enzymatic hydrolysis of whey protein with a proteinase selected from the group consisting of a bacillolysin proteinase and a subtilisin proteinase, wherein the whey protein comprises alpha-lactalbumin, beta-lactoglobulin, serum albumin, immunoglobulins and combinations thereof, and wherein the formulation is administered in an amount to provide at least 50 mg/kg body weight to 1500 mg/kg body weight of the hydrolysate of whey protein.

12. The method of claim 11, wherein the hydrolysate comprises about 15% to 35% of peptides having a molecular weight greater than 5000 Daltons.

* * * * *